United States Patent
Kim et al.

(10) Patent No.: US 9,511,357 B2
(45) Date of Patent: Dec. 6, 2016

(54) AMORPHOUS CALCIUM PHOSPHATE CATALYST FOR USE IN PRODUCTION OF 1,3-BUTADIENE AND METHYL ETHYL KETONE FROM 2,3-BUTANEDIOL, AND METHOD OF PREPARING THE SAME

(71) Applicants: SK Innovation Co., Ltd., Seoul (KR); SK Global Chemical Co., Ltd., Seoul (KR)

(72) Inventors: Hee Soo Kim, Daejeon (KR); Dong Ryul Park, Daejeon (KR); Ho Won Lee, Daejeon (KR)

(73) Assignees: SK INNOVATION CO., LTD., Seoul (KR); SK GLOBAL CHEMICAL CO., LTD., Seoul (KR)

( * ) Notice: Subject to any disclaimer, the term of this patent is extended or adjusted under 35 U.S.C. 154(b) by 0 days.

(21) Appl. No.: 14/600,677

(22) Filed: Jan. 20, 2015

(65) Prior Publication Data

US 2016/0151769 A1 Jun. 2, 2016

(30) Foreign Application Priority Data

Nov. 27, 2014 (KR) .................. 10-2014-0167303

(51) Int. Cl.

| | |
|---|---|
| *C07C 45/00* | (2006.01) |
| *B01J 27/18* | (2006.01) |
| *C01B 25/32* | (2006.01) |
| *C07C 1/20* | (2006.01) |
| *C07C 1/24* | (2006.01) |
| *C07C 5/333* | (2006.01) |
| *C07C 11/167* | (2006.01) |
| *C07C 45/52* | (2006.01) |
| *B01J 37/02* | (2006.01) |
| *B01J 37/03* | (2006.01) |
| *B01J 37/08* | (2006.01) |

(52) U.S. Cl.
CPC ......... *B01J 27/1806* (2013.01); *B01J 37/0236* (2013.01); *C01B 25/322* (2013.01); *C01B 25/324* (2013.01); *C07C 1/20* (2013.01); *C07C 1/24* (2013.01); *C07C 5/333* (2013.01); *C07C 11/167* (2013.01); *C07C 45/52* (2013.01); *B01J 37/031* (2013.01); *B01J 37/08* (2013.01)

(58) Field of Classification Search
CPC .... B01J 27/1806; C07C 45/512; C01B 25/324
USPC ........................................................ 568/404
See application file for complete search history.

(56) References Cited

U.S. PATENT DOCUMENTS

| | | | |
|---|---|---|---|
| 1,841,055 A | 1/1932 | Rappe et al. | |
| 2,386,324 A | 10/1945 | Lorch | |
| 4,363,748 A * | 12/1982 | Crum .................. | B01J 23/10 |
| | | | 502/208 |
| 2010/0143271 A1* | 6/2010 | Yang .................. | A61K 8/24 |
| | | | 424/52 |

FOREIGN PATENT DOCUMENTS

| | | |
|---|---|---|
| KR | 10-1287167 | 2/2011 |
| KR | 1020120099818 A | 12/2012 |
| KR | 10-1298672 B1 | 8/2013 |
| WO | 2009/151342 A1 | 12/2009 |

OTHER PUBLICATIONS

Sergey V. Dorozhkin, "Amorphous calcium (ortho) phosphates," ACTA Biomaterialia, 6:4457-4475 (2010).

* cited by examiner

*Primary Examiner* — Porfirio Nazario Gonzalez
*Assistant Examiner* — Kofi Adzamli
(74) *Attorney, Agent, or Firm* — Abelman, Frayne & Schwab

(57) ABSTRACT

Disclosed are an amorphous calcium phosphate catalyst for use in production of 1,3-butadiene and methyl ethyl ketone from 2,3-butanediol, a preparation method thereof, and a method of producing 1,3-butadiene and methyl ethyl ketone from 2,3-butanediol using the amorphous calcium phosphate catalyst.

7 Claims, 4 Drawing Sheets

AMORPHOUS CALCIUM PHOSPHATE CATALYST FOR USE IN PRODUCTION OF 1,3-BUTADIENE AND METHYL ETHYL KETONE FROM 2,3-BUTANEDIOL, AND METHOD OF PREPARING THE SAME

CROSS-REFERENCE TO RELATED APPLICATION

This application claims the benefit of Korean Patent Application No. 10-2014-0167303, filed Nov. 27, 2014, entitled "Amorphous calcium phosphate catalyst used for 1,3-butadiene and methyl ethyl ketone from 2,3-butanediol and preparation method thereof," which is hereby incorporated by reference in its entirety into this application.

BACKGROUND OF THE INVENTION

1. Technical Field

The present invention relates to an amorphous calcium phosphate catalyst for use in production of 1,3-butadiene and methyl ethyl ketone from 2,3-butanediol, and a method of preparing the same. More particularly, the present invention relates to an amorphous calcium phosphate catalyst containing phosphoric acid and calcium, a preparation method thereof and a method of producing 1,3-butadiene and methyl ethyl ketone from 2,3-butanediol using the amorphous calcium phosphate catalyst.

2. Description of the Related Art 1,3-butadiene is widely utilized as a synthetic rubber material for use in car tires. When it is polymerized with styrene and acrylonitrile, synthetic rubber products such as ABS, NBR and SBR are obtained.

1,3-butadiene is prepared as a byproduct in the course of steam cracking crude oil to obtain ethylene and olefin. It may be prepared via oxidative dehydrogenation of n-butane or butene. In the United States and the Former Soviet Union in the past, an alcohol produced from grain was dehydrogenated and simultaneously condensed in the presence of a metal oxide catalyst, and thus converted into 1,3-butadiene.

In particular, preparation of 1,3-butadiene was under active study by IG Farben in Germany during World War II. The process of producing 1,3-butadiene devised by IG Farben includes converting coal-derived acetylene into acetaldehyde or acetol to prepare 1,3-butanediol that is then reacted in the presence of an acid or base catalyst to thus be converted into 1,3-butadiene.

U.S. Pat. No. 1,984,055 discloses conversion of 1,3-butanediol into 1,3-butadiene using a catalyst comprising sodium hydrogen phosphate, calcium-ammonium phosphate and sodium n-butylamine phosphate. These catalysts are reported to show 1,3-butadiene selectivity of at least 85% and superior durability.

Also, in U.S. Pat. No. 2,386,324, attempts have been made to convert a 1,3-butanediol aqueous solution into 1,3-butadiene using a diammonium phosphate catalyst, leading to a yield of 50% based on evaluation results over 56 days.

Meanwhile, methyl ethyl ketone (MEK) is produced via dehydrogenation from 2-butanol using a catalyst such as Cu or Zn, and may be obtained via a liquid oxidation reaction of a carbon compound resulting from a Fischer-Tropsch process or a heavy naphtha process.

Recently, techniques for converting 2,3-butanediol produced via fermentation into 1,3-butadiene are known, in addition to intermediate products obtained from petrochemical processes. International Publication No. WO 2009151342 discloses production of 2,3-butanediol from syngas via microorganism fermentation, and the produced 2,3-butanediol may be converted into 1,3-butadiene and methyl ethyl ketone using a catalyst.

Korean Patent Application Publication No. 10-2012-0099818 discloses the use of a cesium oxide-silica catalyst so that a sum of 1,3-butadiene and methyl ethyl ketone selectivity is 95% in the temperature range of 400~500° C.

Meanwhile, Korean Patent No. 1287167 discloses preparation of calcium phosphate catalysts having hydroxyapatite (HAP) and calcium pyrophosphate structures and combinations thereof. These catalysts are calcium phosphate compounds represented by $Ca_5(PO_4)_3OH$ and $Ca_2(P_2O_7)$ with specific crystalline structures. When such catalysts are thermally treated at 300~700° C. and applied at a temperature of 380° C. and a pressure of 2 atm, 1,3-butadiene is produced in an amount of 25.2% under the condition that a maximum amount of methyl ethyl ketone is 64.5%. Furthermore, when 1,3-butadiene is produced in a maximum amount of 37.4%, methyl ethyl ketone is obtained in a maximum amount of 50.4%.

Korean Patent No. 1298672 discloses addition of alumina to hydroxyapatite to increase 1,3-butadiene selectivity, and thus the 1,3-butadiene selectivity is reported to be 61% based on the reaction results at 360° C. In these patents, the calcium phosphate catalyst has a hydroxyapatite structure or a calcium pyrophosphate structure.

A calcium phosphate catalyst is known to be formed in various phases, depending on the kind of precursor used for catalyst preparation, pH upon catalyst synthesis and control thereof, and the ratio of Ca to P therein.

Calcium phosphate phases are mentioned by Acta Biomaterialia 6 (2010) 4457. Calcium phosphates may include, depending on the ratio of Ca to P therein, monocalcium phosphate ($Ca(H_2PO_4)_2$, Ca/P=0.5), dicalcium phosphate ($CaHPO_4$, Ca/P=1.0), tricalcium phosphate ($Ca_3(PO_4)_2$, Ca/P=1.50), octacalcium phosphate ($Ca_8(HPO_4)_2(PO_4)_4$, Ca/P=1.33), hydroxyapatite ($Ca_5(PO_4)_3(OH)$, Ca/P=1.67), and amorphous calcium phosphate ($Ca_xH_y(PO_4)_z \cdot nH_2O$ n=3~4.5, 15~20% $H_2O$). Furthermore, mutual phase transformation is known to occur during thermal treatment after preparation of the catalyst.

SUMMARY OF THE INVENTION

Therefore, an embodiment of the present invention is intended to provide a method of preparing a catalyst that may increase 2,3-butanediol conversion and 1,3-butadiene selectivity upon production of 1,3-butadiene and methyl ethyl ketone (MEK) from 2,3-butanediol.

Also, an embodiment of the present invention is intended to provide a method of producing 1,3-butadiene and methyl ethyl ketone from 2,3-butanediol using a catalyst prepared by the method as above.

Also, an embodiment of the present invention is intended to provide a catalyst for use in production of 1,3-butadiene and methyl ethyl ketone from 2,3-butanediol (MEK).

Also, an embodiment of the present invention is intended to provide a method of producing 1,3-butadiene and methyl ethyl ketone from 2,3-butanediol using the catalyst as above.

In accordance with an embodiment thereof the present invention provides a method of preparing an amorphous calcium phosphate catalyst for use in production of 1,3-butadiene and methyl ethyl ketone from 2,3-butanediol, comprising: (a) reacting a phosphoric acid-containing solution with an alkali, thus preparing a phosphoric acid-alkali aqueous solution; (b) adding the phosphoric acid-alkali aqueous solution with a calcium precursor aqueous solution, thus preparing a calcium phosphate slurry; and (c) thermally treating the slurry, thus obtaining an amorphous calcium phosphate catalyst.

In an exemplary embodiment, in (a), the phosphoric acid-containing solution may comprise at least one selected from the group consisting of orthophosphoric acid ($H_3PO_4$), pyrophosphoric acid ($H_4P_2O_7$), tripolyphosphoric acid ($H_5P_3O_{10}$), and tetrapolyphosphoric acid ($H_6P_4O_{13}$).

In an exemplary embodiment, preparing the calcium phosphate slurry in (b) may be performed at a pH of higher than 5.0 but less than 11.0.

In an exemplary embodiment, in (b), a Ca/P ratio may be 1.20-1.67.

In an exemplary embodiment, in (b), a Ca/P ratio may be 1.20-1.30.

In an exemplary embodiment, in (b), the calcium precursor may comprise at least one selected from the group consisting of calcium acetate ($Ca(CH_3COO)_2$), calcium nitrate ($Ca(NO_3)_2$), and calcium chloride ($CaCl_2$).

In an exemplary embodiment, thermally treating may be performed at 400-600° C. for 1-10 hr.

In accordance with another embodiment thereof, the present invention provides an amorphous calcium phosphate catalyst for use in production of 1,3-butadiene and methyl ethyl ketone from 2,3-butanediol.

In an exemplary embodiment, the amorphous calcium phosphate catalyst may have a Ca/P ratio of 1.20-1.67.

In an exemplary embodiment, the amorphous calcium phosphate catalyst may have a Ca/P ratio of 1.20-1.30.

In accordance with still another embodiment thereof the present invention provides a method of producing 1,3-butadiene and methyl ethyl ketone from 2,3-butanediol using a catalyst prepared by the method as above.

In accordance with yet another embodiment thereof the present invention provides a method of producing 1,3-butadiene and methyl ethyl ketone from 2,3-butanediol using the amorphous calcium phosphate catalyst as above.

According to embodiments of the present invention, it is possible to prepare a catalyst that results in high 2,3-butanediol conversion and high 1,3-butadiene selectivity. According to embodiments of the present invention, the lifetime of the catalyst can be improved by adjusting acid strength using a calcium phosphate catalyst having both acid and base properties, and high catalytic activity can be maintained even under long-term stability.

DESCRIPTION OF SPECIFIC EMBODIMENTS

Figure 1:
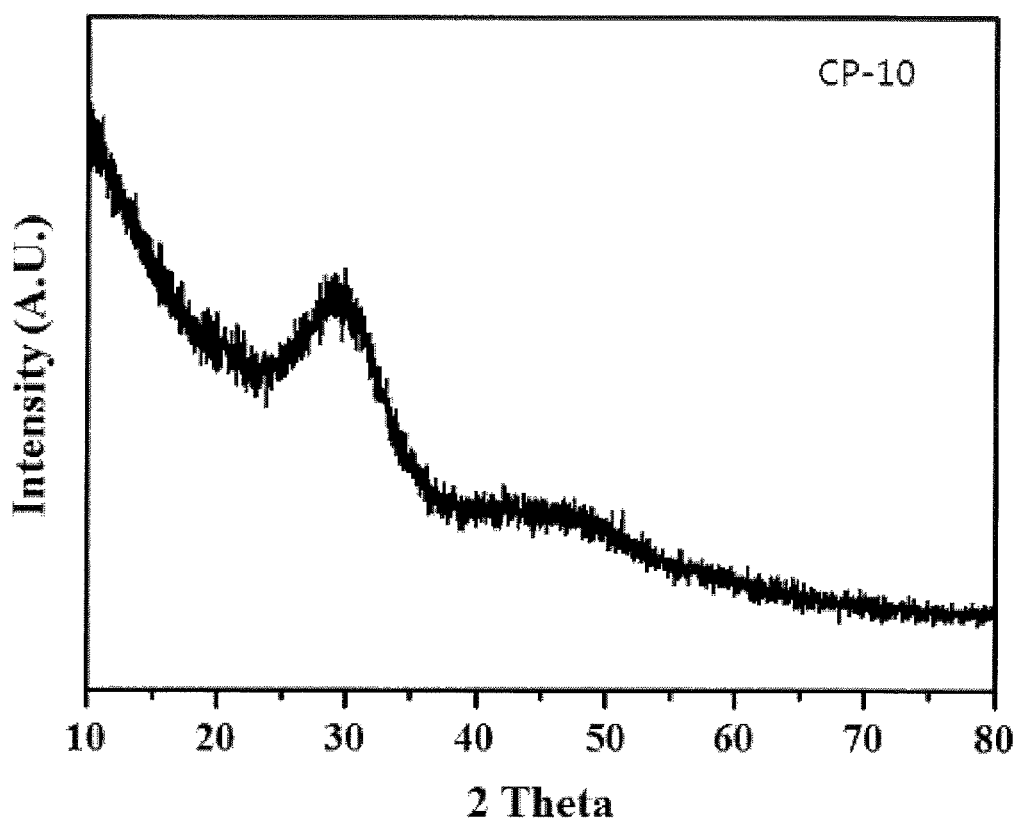
FIG. 1 illustrates the results of X-ray diffraction (XRD) analysis of a calcium phosphate catalyst (CP-10) of Preparation Example 1.

The present invention may be embodied by the following description. The following description is to be understood as disclosing embodiments of the present invention, and the present invention is not necessarily limited thereto.

An embodiment of the present invention addresses an amorphous calcium phosphate catalyst for use in production of 1,3-butadiene and methyl ethyl ketone from 2,3-butanediol.

As used herein, the term "amorphous" in the amorphous calcium phosphate catalyst refers to any structure having no specific crystalline structure, unlike a crystal structure such as a hydroxyapatite structure or a calcium phosphate structure.

In the calcium phosphate catalyst, calcium phosphate refers to a catalyst containing calcium and phosphate, and examples thereof may include monocalcium phosphate, dicalcium phosphate, tricalcium phosphate, octacalcium phosphate, hydroxyapatite, and calcium pyrophosphate.

Korean Patent No. 1287167 discloses a calcium phosphate catalyst for use in production of 1,3-butadiene and methyl ethyl ketone from 2,3-butanediol, but merely describes crystalline structures of hydroxyapatite and calcium pyrophosphate as the calcium phosphate catalyst.

However, the present inventors have confirmed that 1,3-butadiene selectivity is higher when using the amorphous calcium phosphate catalyst than when using the crystalline calcium phosphate catalyst having hydroxyapatite and calcium pyrophosphate structures.

In the calcium phosphate catalyst, a Ca/P ratio plays an important role in determining the calcium phosphate structure and also determining properties of acid and base present in the catalyst.

As crystalline calcium phosphate, hydroxyapatite has a Ca/P ratio of 1.67, and calcium pyrophosphate has a Ca/P ratio of 1.0. Since hydroxyapatite has a molecular formula of $Ca_5(PO_4)_3(OH)$, Ca/P becomes 5Ca/3P, so that Ca/P equals 1.67. For calcium pyrophosphate having a molecular formula of $Ca_2P_2O_7$, Ca/P equals 1.0.

The calcium phosphate catalyst has both acid and base properties. As the Ca/P ratio is close to 1.67 corresponding to the hydroxyapatite structure, the amount of Ca in the catalyst may increase, which means that base properties may be relatively strong.

On the other hand, in the catalyst having a Ca/P ratio close to 1.0 corresponding to the calcium pyrophosphate structure, the acid strength of the catalyst is relatively strong. The amorphous calcium phosphate catalyst having a Ca/P ratio of 1.20-1.30 means that the amounts of acid and base are balanced.

In an exemplary embodiment of the present application, the amorphous calcium phosphate has a Ca/P ratio of 1.20-1.67, and preferably 1.20-1.30.

Another embodiment of the present invention addresses a method of preparing an amorphous calcium phosphate catalyst for use in production of 1,3-butadiene and methyl ethyl ketone from 2,3-butanediol.

The reaction for producing 1,3-butadiene and methyl ethyl ketone (MEK) from 2,3-butanediol is schematically as follows.

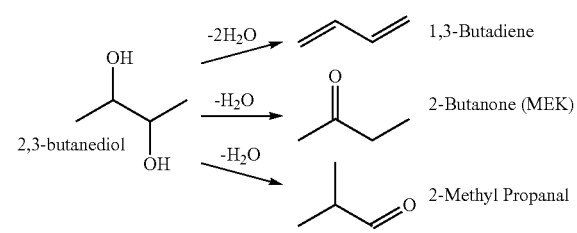

When 2,3-butanediol is reacted in the presence of an acid or base catalyst, not only 1,3-butadiene as a main product but also methyl ethyl ketone and 2-methylpropane aldehyde as byproducts are obtained. Individual products are converted via complicated mechanisms. In particular, 1,3-butadiene may be maximized in selectivity only under the condition that the catalyst has base properties as well as the acid properties.

The reaction for producing 1,3-butadiene and methyl ethyl ketone (MEK) from 2,3-butanediol is a dehydration reaction. The catalyst for use in dehydration should have both acid and base properties therein.

In the embodiment of the present invention, the method of preparing an amorphous calcium phosphate catalyst for use in production of 1,3-butadiene and methyl ethyl ketone from 2,3-butanediol includes (a) reacting a phosphoric acid-containing solution with an alkali, thus preparing a phosphoric acid-alkali aqueous solution, (b) adding the phosphoric acid-alkali aqueous solution with a calcium precursor aqueous solution, thus preparing a calcium phosphate slurry, and (c) thermally treating the slurry, thus obtaining an amorphous calcium phosphate catalyst.

In (a), the phosphoric acid-containing solution is reacted with an alkaline salt, thus preparing the phosphoric acid-alkali aqueous solution. The phosphoric acid-containing solution may include at least one selected from among orthophosphoric acid ($H_3PO_4$), pyrophosphoric acid ($H_4P_2O_7$), tripolyphosphoric acid ($H_5P_3O_{10}$), and tetrapolyphosphoric acid ($H_6P_4O_{13}$). Preferably useful is phosphoric acid or pyrophosphoric acid, and more preferably useful is pyrophosphoric acid.

In (a), the alkali may be a strong base such as NaOH, or a weak base such as ammonia. Preferably useful is a weak base, and more preferably useful is ammonia.

In (b), the phosphoric acid-alkali aqueous solution is added with the calcium precursor aqueous solution, thus preparing the calcium phosphate slurry.

The calcium precursor may include calcium chloride, calcium nitrate, or calcium acetate, and is not particularly limited but may be calcium acetate.

In (b), the Ca/P ratio is 1.20-1.67. If this ratio falls out of the above range, 1,3-butadiene selectivity may remarkably decrease. Particularly, the Ca/P ratio may be set to 1.20-1.30.

In (b), calcium phosphate is prepared at a pH of higher than 5 but less than 11, and preferably pH 6~10. When the pH is 5.0 or less or 11.0 or more, an excess of nitric acid or phosphoric acid and ammonia or NaOH are required, and an amorphous catalyst may not be formed.

In (c), the calcium phosphate slurry obtained in (b) is thermally treated. Thermal treatment is performed at 500° C. for 6 hr, and is not particularly limited but may be carried out at 400-600° C. for 1-10 hr. If the thermal treatment temperature is higher than 600° C., a crystalline structure such as calcium pyrophosphate may be formed.

Yet another embodiment of the present invention addresses a method of producing 1,3-butadiene and methyl ethyl ketone from 2,3-butanediol via dehydration using the amorphous calcium phosphate catalyst as above.

Still another embodiment of the present invention addresses a method of producing 1,3-butadiene and methyl ethyl ketone from 2,3-butanediol via dehydration using an amorphous calcium phosphate catalyst prepared by the method as above.

As such, the dehydration may be carried out at a reaction temperature of 300~400° C., a reaction pressure of 0~50 bar and a weight hourly space velocity (WHSV) of 0.01-10.0 $h^{-1}$.

A better understanding of the present invention may be obtained via the following examples which are set forth to illustrate, but are not to be construed as limiting the present invention.

Preparation Example 1

Preparation of Amorphous Calcium Phosphate Catalyst (CP-10)

8.62 g of $H_4P_2O_7$ was dissolved in deionized water, thus preparing 200 mL of a diluted pyrophosphoric acid aqueous solution, which was then added with 37.60 g of 28 wt % $NH_4OH$ aqueous solution, followed by stirring for 30 min (Solution A). Separately, 23.74 g of $Ca(OAc)_2$ was dissolved in deionized water, thus obtaining 150 mL of a calcium precursor aqueous solution (Solution B). To Solution A, Solution B was slowly added at a rate of 3.5 mL/min at room temperature for 30 min, giving a calcium phosphate slurry solution (Solution C). Solution C as the mixed slurry solution was maintained at a pH of about 10.0, and was sufficiently stirred for 24 hr and then purified by filtration with 2 L of deionized water, thus obtaining a solid product in cake form. The calcium phosphate cake was dried at 80° C. for 6 hr, ground, sorted and thermally treated at 500° C. for 6 hr, yielding a calcium phosphate catalyst.

Via XRD analysis, the amounts of Ca and P in the prepared catalyst were measured, and the nature of the catalyst was determined. The CP-10 catalyst of Preparation Example 1 had a Ca/P ratio of 1.23, and was analyzed to be amorphous calcium phosphate via XRD. FIG. 1 illustrates the results of XRD analysis of the CP-10 catalyst.

Preparation Example 2

Preparation of Amorphous Calcium Phosphate Catalyst (CP-6)

Solutions A, B and C were prepared in the same manner as in Preparation Example 1, with the exception that the pH of Solution C as the mixed slurry solution was maintained at about 6.

The pH of Solution C was adjusted to 6 by adding $H_4P_2O_7$ following addition of the calcium precursor aqueous solution, after which filtration, purification and firing were performed in the same manner as in Preparation Example 1 while the pH was maintained at 6.0, thereby preparing a catalyst, called CP-6.

Preparation Example 3

Preparation of Amorphous Calcium Phosphate Catalyst (CP-8)

Solutions A, B and C were prepared in the same manner as in Preparation Example 1, with the exception that the pH of Solution C as the mixed slurry solution was maintained at about 8.

The pH of Solution C was adjusted to 8 by adding $H_4P_2O_7$ following addition of the calcium precursor aqueous solution, after which filtration, purification and firing were performed in the same manner as in Preparation Example 1 while the pH was maintained at 8.0, thereby preparing a catalyst, called CP-8.

Figure 2:
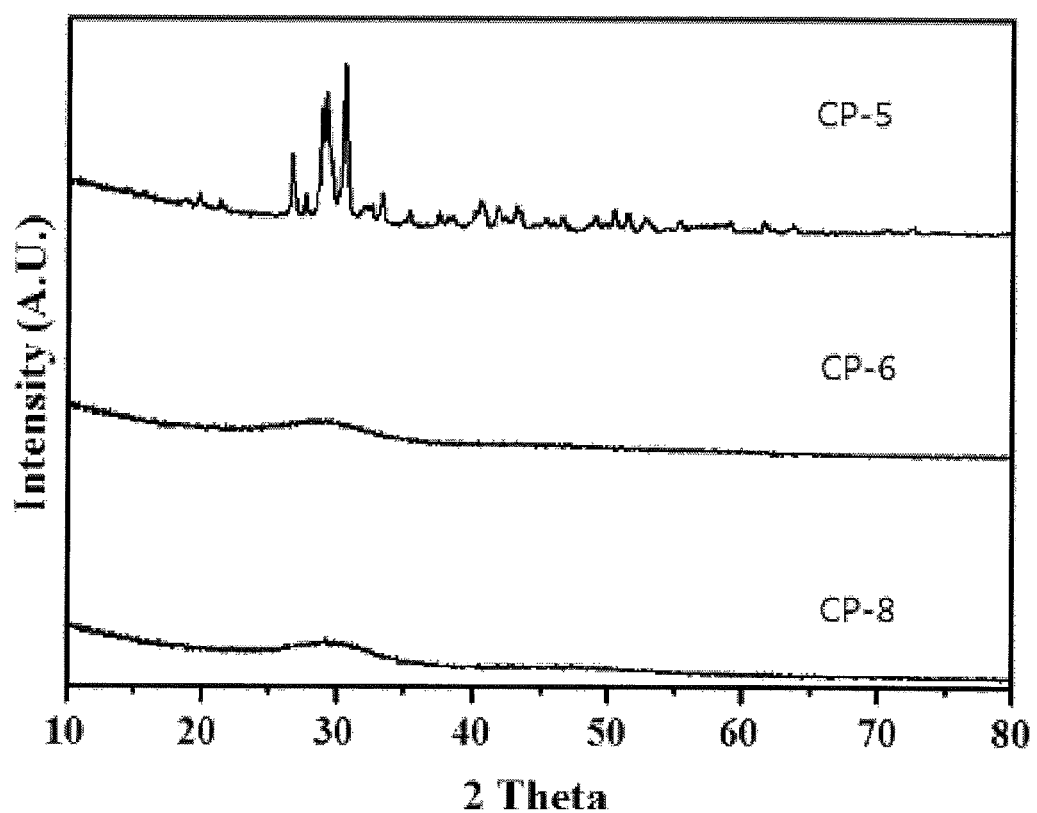
FIG. 2 illustrates the results of XRD analysis of calcium phosphate catalysts of Preparation Example 2 (CP-6), Preparation Example 3 (CP-8) and Comparative Preparation Example 3 (CP-5)
Figure 3:
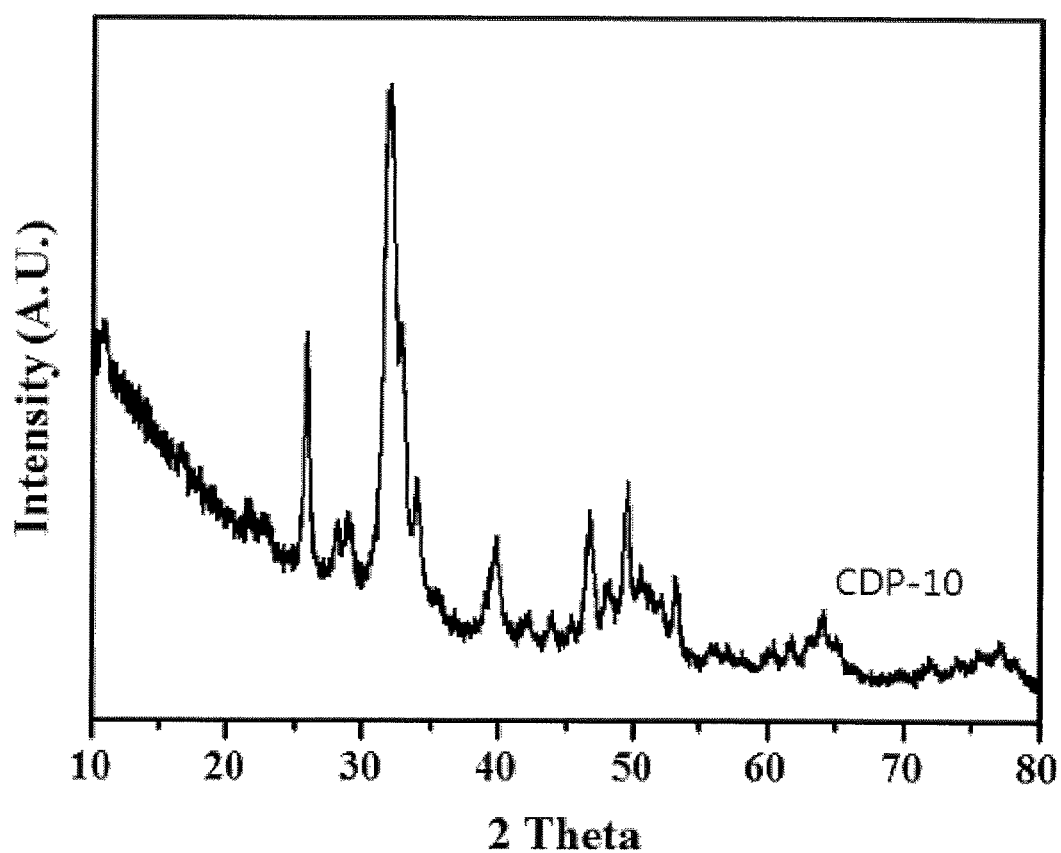
FIG. 3 illustrates the results of XRD analysis of a calcium phosphate catalyst (CDP-10) of Comparative Preparation Example 1.
Figure 4:
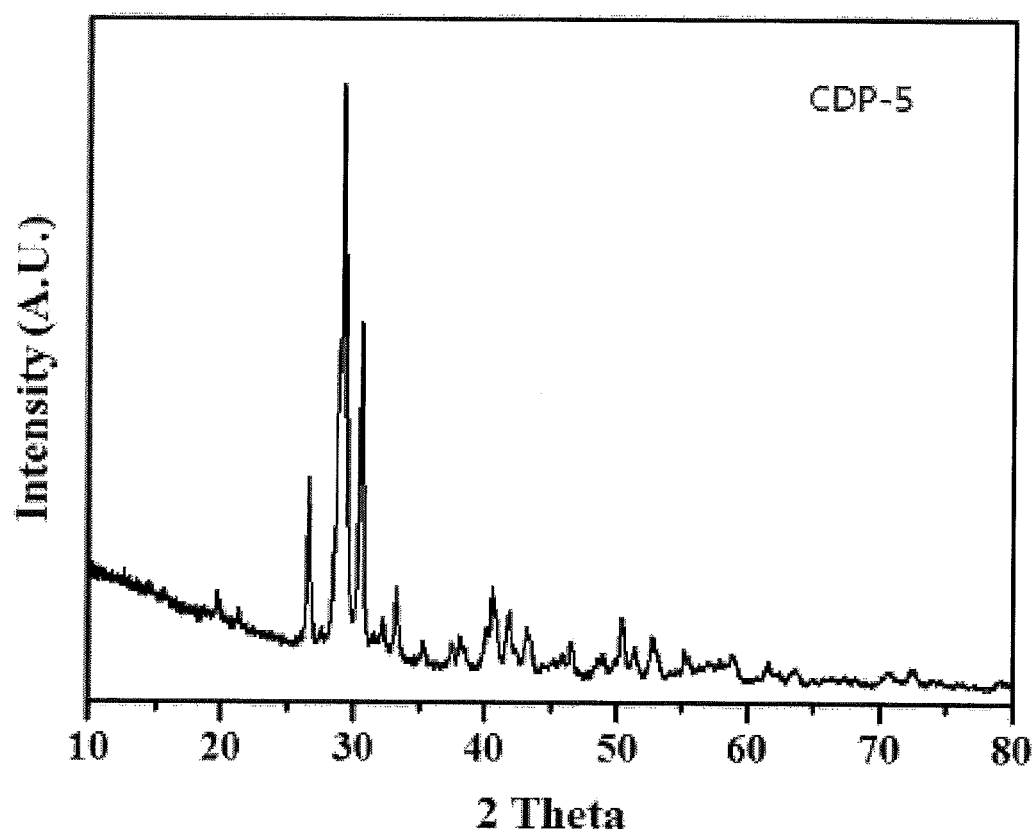
FIG. 4 illustrates the results of XRD analysis of a calcium phosphate catalyst (CDP-5) of Comparative Preparation Example 2.

FIG. 2 illustrates the results of XRD analysis of CP catalysts obtained in Preparation Examples 2 and 3 and Comparative Preparation Example 3. In the CP-6 and CP-8 catalysts other than the CP-5 catalyst, the peaks corresponding to amorphous characteristics were observed.

Preparation Example 4

Preparation of Amorphous Calcium Phosphate Catalyst (CP-10-600)

A catalyst, called CP-10-600, was prepared in the same manner as in Preparation Example 1, with the exception that the calcium phosphate cake was thermally treated at 600° C. for 6 hr, instead of thermal treatment at 500° C. for 6 hr following drying at 80° C. for 6 hr, grinding and sorting in Preparation Example 1. This catalyst was called a CP-10-600 catalyst. CP-10-600 was determined to be an amorphous calcium phosphate catalyst.

Preparation Example 5

Preparation of Amorphous Calcium Phosphate Catalyst (CPN-10)

A calcium phosphate catalyst was prepared in the same manner as in Preparation Example 1, with the exception that 150 mL of an aqueous solution (Solution B) was prepared by dissolving 35.44 g of $Ca(NO_3)_2$ in deionized water, instead of preparation of 150 mL of an aqueous solution as Solution B by dissolving 23.74 g of $Ca(OAC)_2$ in deionized water in Preparation Example 1.

Preparation Example 6

Preparation of Amorphous Calcium Phosphate Catalyst (CPC-10)

A calcium phosphate catalyst was prepared in the same manner as in Preparation Example 1, with the exception that 150 mL of an aqueous solution (Solution B) was prepared by dissolving 22.06 g of $Ca(Cl)_2$ in deionized water, instead of preparation of 150 mL of an aqueous solution as Solution B by dissolving 23.74 g of $Ca(OAC)_2$ in deionized water in Preparation Example 1.

Comparative Preparation Example 1

Preparation of Calcium Phosphate Catalyst Having Hydroxyapatite Structure (CDP-10)

35.44 g of $Ca(NO_3)_2 4H_2O$ was dissolved in 200 mL of deionized water and $NH_4OH$ was slowly added so that the pH of the aqueous solution was maintained at 10.0 (Solution A). Separately, 11.89 g of diammonium hydrogen phosphate was dissolved in 200 mL of deionized water to give a phosphate aqueous solution, the pH of which was maintained at 10.0 with $NH_4OH$ (Solution B). While Solution B was added to Solution A, the pH of the mixed solution was maintained at 10.0 with $HNO_3$ or $NH_4OH$. The mixed slurry solution was sufficiently stirred for 24 hr, and purified by filtration with 2 L of deionized water, thus obtaining a solid product in cake form. The calcium phosphate cake was dried at 80° C. for 24 hr, ground, sorted and thermally treated at 500° C. for 6 hr, yielding a calcium phosphate catalyst.

Comparative Preparation Example 2

Preparation of Catalyst Having Calcium Pyrophosphate Structure (CDP-5)

35.44 g of $Ca(NO_3)_2 4H_2O$ was dissolved in 200 mL of deionized water and $HNO_3$ was slowly added so that the pH of the aqueous solution was maintained at 5.0 (Solution A). Separately, 11.89 g of diammonium hydrogen phosphate was dissolved in 200 mL of deionized water to give a phosphate aqueous solution, the pH of which was maintained at 5.0 with $HNO_3$ (Solution B). While Solution B was added to Solution A, the pH of the mixed solution was maintained at 5.0 with $HNO_3$ or $NH_4OH$. The mixed slurry solution was sufficiently stirred for 24 hr, and purified by filtration with 2 L of deionized water, thus obtaining a solid product in cake form. The calcium phosphate cake was dried at 80° C. for 24 hr, ground, sorted and thermally treated at 500° C. for 6 hr, yielding a calcium phosphate catalyst.

Comparative Preparation Example 3

Preparation of Catalyst Having Calcium Pyrophosphate Structure (CP-5)

Solutions A, B and C were prepared in the same manner as in Preparation Example 1, with the exception that the pH of Solution C as the mixed slurry solution was maintained at about 5.

The pH of Solution C was adjusted to 5 by adding $H_4P_2O_7$ following addition of the calcium precursor aqueous solution, after which filtration, purification and firing were performed in the same manner as in Preparation Example 1 while the pH was maintained at 5.0, thereby preparing a catalyst, called CP-5.

The CP-5 catalyst of Comparative Preparation Example 3 had a Ca/P ratio of 1.0, and was analyzed to have a calcium pyrophosphate ($Ca_2P_2O_7$) structure, unlike the CP-10 catalyst.

As mentioned above, FIG. 2 illustrates the results of XRD analysis of the CP-5 catalyst of Comparative Preparation Example 3. As illustrated in FIG. 2, the CP-5 catalyst was crystalline.

Examples 1 to 6 and Comparative Examples 1 to 6

Using the catalysts of Preparation Examples 1 to 6 and Comparative Preparation Examples 1 to 3, conversion reaction of 2,3-butanediol (2,3-BDO) into 1,3-butadiene (1,3-BD) according to embodiments of the present invention was carried out.

Comparative Example 4 was evaluated under the same reaction conditions as in Comparative Preparation Examples 1 to 3, with the exception that a commercially available reagent calcium pyrophosphate was used after thermal treatment at 500° C., instead of the catalysts of Comparative Preparation Examples 1 to 3.

Comparative Example 5 was evaluated under the same reaction conditions as in Comparative Preparation Examples 1 to 3, with the exception that a typical acid catalyst H-ZSM-5 was used, instead of the catalysts of Comparative Preparation Examples 1 to 3.

Comparative Example 6 was evaluated under the same reaction conditions as in Comparative Preparation Examples 1 to 3, with the exception that a commercially available base catalyst CaO was used, instead of the catalysts of Comparative Preparation Examples 1 to 3.

Dehydration of 2,3-butanediol was evaluated using a self-made continuous flow reactor having a fixed catalyst bed, and the feed before reaction was passed through a preheating zone at 300° C., and allowed to react under conditions of atmospheric pressure, $N_2$ at 10 cc/min, 360° C., and WHSV=0.5 $h^{-1}$.

The results of evaluation of the prepared catalysts are shown in Table 1 below. All the products obtained after catalysis were vaporized and analyzed via on-line gas chromatography (GC). The main products were composed of 1,3-butadiene, methyl ethyl ketone (MEK) and $H_2O$, and small amounts of byproducts included butene, 2-methylpropanealdehyde, 3-buten-2-ol, and 2-methylpropanol. The 2,3-butanediol conversion, 1,3-butadiene selectivity and methyl ethyl ketone selectivity were calculated based on mole balance. Supposing that 2,3-butanediol is 100% converted into 1,3-butadiene upon calculation based on mass %, about 40 wt % of water is theoretically produced. The amount of $H_2O$ in the evaluated catalyst was measured to be about 20~30 wt %.

In Comparative Example 4 using calcium pyrophosphate ($Ca_2P_2O_7$) as a commercially available reagent, low 1,3-butadiene selectivity was exhibited compared to the calcium pyrophosphate catalyst of Comparative Preparation Example 2. The reason why 1,3-butadiene selectivity is low despite the same calcium pyrophosphate structure is that acid and base properties of the catalyst have an influence on the selectivity, in addition to the structural effect.

In Comparative Example 5 using a typical acid catalyst H-ZSM-5, relatively low 2,3-butanediol conversion and low 1,3-butadiene selectivity were manifested. In Comparative Example 6 using a commercially available reagent CaO as a base catalyst, 2,3-butanediol conversion and 1,3-butadiene selectivity were remarkably low.

TABLE 1

| Example | Prep. Example | Catalyst | Ca/P | Catalyst Nature | 2,3-BDO Conversion (%) | 1,3-BD Selectivity (%) | MEK Selectivity (%) |
|---|---|---|---|---|---|---|---|
| Ex. 1 | Prep. 1 | CP-10 | 1.23 | Amorphous | 100 | 62.1 | 29.8 |
| Ex. 2 | Prep. 2 | CP-6 | 1.21 | Amorphous | 100 | 54.5 | 36.6 |
| Ex. 3 | Prep. 3 | CP-8 | 1.22 | Amorphous | 100 | 58.4 | 31.7 |
| Ex. 4 | Prep. 4 | CP-10-600 | 1.24 | Amorphous | 100 | 56.7 | 33.2 |
| Ex. 5 | Prep. 5 | CPN-10 | 1.23 | Amorphous | 100 | 54.1 | 37.3 |
| Ex. 6 | Prep. 6 | CPC-10 | 1.21 | Amorphous | 100 | 51.1 | 33.1 |
| C. Ex. 1 | C. Prep. 1 | CDP-10 | 1.67 | Hydroxyapatite | 99.4 | 18.1 | 57.1 |
| C. Ex. 2 | C. Prep. 2 | CDP-5 | 1.0 | Calcium pyrophosphate | 98.7 | 48.7 | 33.6 |
| C. Ex. 3 | C. Prep. 3 | CP-5 | 1.0 | Calcium pyrophosphate | 100 | 46.3 | 35.5 |
| C. Ex. 4 | Reagent | $Ca_2P_2O_7$ | 1.0 | Calcium pyrophosphate | 91.3 | 9.8 | 29.7 |
| C. Ex. 5 | Commercial Catalyst | H-ZSM-5 | | | 79.0 | 8.4 | 48.0 |
| C. Ex. 6 | Reagent | CaO | | | 84.0 | 6.4 | 31.0 |

In Example 1, the CP-10 catalyst exhibited relatively high 1,3-butadiene selectivity, and the nature of the catalyst was considered to affect the 1,3-butadiene selectivity. The present inventors prepared a calcium phosphate catalyst having another phase via Comparative Preparation Example 1. In Comparative Example 1, the catalyst of Comparative Preparation Example 1 was analyzed to have a hydroxyapatite structure via XRD.

To compare the results of 1,3-butadiene selectivity depending on the calcium phosphate structure, a calcium phosphate catalyst having another structure was prepared in Comparative Preparation Example 2. The same calcium precursor as in Comparative Preparation Example 1 was used in the same amount, and Solutions A, B and C were prepared at pH 5, instead of pH 10. The prepared catalyst was analyzed to be a calcium phosphate catalyst having a crystalline calcium pyrophosphate structure via XRD.

In Comparative Example 2, the crystalline catalyst of Comparative Preparation Example 2 exhibited low 1,3-butadiene selectivity, compared to the amorphous catalyst of the present application.

In Comparative Preparation Example 3, the catalyst was prepared in the same manner as in Preparation Example 1, with the exception that the pH was adjusted to 5. In Comparative Example 3, the catalyst of Comparative Preparation Example 3 was analyzed to be calcium pyrophosphate via XRD, with a Ca/P ratio of 1.0.

In Comparative Example 3, the calcium pyrophosphate catalyst of Comparative Preparation Example 3 exhibited slightly low 1,3-butadiene selectivity compared to the amorphous calcium phosphate catalyst but high selectivity compared to the calcium phosphate catalyst having a hydroxyapatite structure.

Based on such results, both acid and base functions of the catalyst are considered to affect the 1,3-butadiene conversion. Hence, it is important to control not only the calcium phosphate structure but also the acid and base properties.

Comparative Examples 7 to 16

In Comparative Examples 7 to 16, acid and base catalysts for use in production of olefin from alcohol were utilized to prepare 1,3-butadiene (1,3-BD) from 2,3-butanediol (2,3-BDO).

In Comparative Examples 7 to 16, the acid or base catalysts for use in converting 2,3-BDO could be applied to commercialization processes, and were known to have typical acid or base properties.

The 1,3-butadiene conversion reaction by the commercially available catalysts was evaluated under conditions of 350~400° C., WHSV=0.5 $h^{-1}$ and atmospheric pressure after loading of the catalyst to a continuous flow reactor having a fixed catalyst bed. 2,3-BDO as the feed before reaction was passed through a preheating zone of 300° C. and then introduced into the catalyst bed, and a carrier gas $N_2$ was injected at 10 cc/min upon reaction.

The catalysis results are shown in Table 2 below. Most of the commercially available catalysts having acid or base properties exhibited high MEK selectivity and low 1,3-BD selectivity.

TABLE 2

| C. Ex. | Catalyst | Reaction Temp. (° C.) | 2,3-BDO Conversion (%) | 1,3-BD Selectivity (%) | MEK Selectivity (%) |
|---|---|---|---|---|---|
| 7 | $Al_2O_6$ | 350 | 99 | 19.2 | 56 |
| 8 | Aluminum Phosphate | 350 | 32 | 3.5 | 56.3 |
| 9 | Silica Aluminum Phosphate | 350 | 69 | 8.1 | 67.2 |
| 10 | γ-Type zeolite | 350 | 95 | 3.4 | 65.1 |
| 11 | Silica-Alumina | 350 | 99 | 17.6 | 45.2 |
| 12 | Titanium silicate | 400 | 21 | 1.1 | 57.0 |
| 13 | $TiO_2$ | 400 | 99 | 9.6 | 46.4 |
| 14 | $ZrO_2$ | 400 | 92 | 9.3 | 63.2 |
| 15 | Hydrotalcite | 400 | 92 | 4.0 | 54.1 |
| 16 | $CeO_2$ | 400 | 60 | 1.1 | 58.3 |

Accordingly, modifications or variations of the present invention may be easily utilized by those having ordinary knowledge in the art, and should also be understood as falling within the scope of the present invention.

What is claimed is:

1. A method of preparing an amorphous calcium phosphate catalyst for use in production of 1,3-butadiene and methyl ethyl ketone from 2,3-butanediol, comprising:
    (a) reacting a phosphoric acid-containing solution with ammonium hydroxide, thus preparing a phosphoric acid-alkali aqueous solution;
    (b) adding the phosphoric acid-alkali aqueous solution with a calcium precursor aqueous solution, thus preparing a calcium phosphate slurry, wherein preparing the calcium phosphate slurry in (b) is performed at a pH of 6-10; and
    (c) thermally treating the slurry, thus obtaining an amorphous calcium phosphate catalyst used for 1,3-butadiene and methyl ethyl ketone from 2,3-butanediol.

2. The method of claim 1, wherein in (a), the phosphoric acid-containing solution comprises at least one selected from the group consisting of orthophosphoric acid ($H_3PO_4$), pyrophosphoric acid ($H_4P_2O_7$), tripolyphosphoric acid ($H_5P_3O_{10}$), and tetrapolyphosphoric acid ($H_6P_4O_{13}$).

3. The method of claim 1, wherein in (b), a Ca/P ratio is 1.20-1.67.

4. The method of claim 1, wherein in (b), a Ca/P ratio is 1.20-1.30.

5. The method of claim 1, wherein in (b), the calcium precursor comprises at least one selected from the group consisting of calcium acetate ($Ca(CH_3COO)_2$), calcium nitrate ($Ca(NO_3)_2$), and calcium chloride ($CaCl_2$).

6. The method of claim 1, wherein thermally treating in (c) is performed at 400-600° C. for 1-10 hr.

7. The method of claim 1, further comprising producing 1,3-butadiene and methyl ethyl ketone from 2,3-butanediol using the amorphous calcium phosphate catalyst produced in step (c).

* * * * *